(12) United States Patent
Lee et al.

(10) Patent No.: US 7,344,837 B2
(45) Date of Patent: Mar. 18, 2008

(54) PCR PRIMER SET FOR DETECTING HEPATITIS B VIRUS, METHOD FOR DETECTING HEPATITIS B USING THE PRIMER SET, AND HEPATITIS B VIRUS DETECTION KIT INCLUDING THE PRIMER SET

(75) Inventors: Young-sun Lee, Gyeonggi-do (KR); Jung-im Han, Seoul (KR); Jung-joo Hwang, Gyeonggi-do (KR); Mi-kyung Kim, Daejeon-si (KR); Yoon-kyoung Cho, Gyeonggi-do (KR); Hee-kyun Lim, Gyeonggi-do (KR); Young-a Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 312 days.

(21) Appl. No.: 10/918,000

(22) Filed: Aug. 13, 2004

(65) Prior Publication Data

US 2005/0037414 A1 Feb. 17, 2005

(30) Foreign Application Priority Data

Aug. 14, 2003 (KR) .................. 10-2003-0056432

(51) Int. Cl.
*C12Q 1/70* (2006.01)

(52) U.S. Cl. ........................... 435/6; 435/91.2

(58) Field of Classification Search .................. None
See application file for complete search history.

(56) References Cited

U.S. PATENT DOCUMENTS 6,197,498 B1 * 3/2001 Koster .................... 435/5

FOREIGN PATENT DOCUMENTS

| EP | 1 312 683 A2 | 5/2003 |
|---|---|---|
| WO | WO 93/23567 | 11/1993 |
| WO | WO 95/02690 | 1/1995 |
| WO | WO 01/68921 A2 | 9/2001 |

OTHER PUBLICATIONS

Buck (Biotechniques (1999) 27(3):528-536).*
Uchida et al. (Journal of Medical Virology, 1995, vol. 45, p. 247-252).*
BLAST alignments—3 pages—Dec. 22, 2006.*
Genbank entry D16666, Hepatitis B virus sequence—Dec. 22, 2006.*
STIC sequence alignments—3 pages—Nov. 3, 2006.*
Wakita et al. (Journal of Clinical Investigation, 1991, vol. 88, p. 1793-1801).*
Office Action from Korean Intellectual Property Office for Application No. 10-2003-0056432 dated Jul. 27, 2005.

(Continued)

*Primary Examiner*—Gary Benzion
*Assistant Examiner*—Stephanie K. Mummert
(74) *Attorney, Agent, or Firm*—Cantor Colburn LLP

(57) ABSTRACT

Provided are a primer set selected from the group consisting of primers having nucleotide sequences as set forth in SEQ ID NOS: 1–40, a method for detecting hepatitis B virus by polymerase chain reaction (PCR) using the primer set, and a hepatitis B virus detection kit including the primer set.

9 Claims, 7 Drawing Sheets

OTHER PUBLICATIONS

European Search Report of Corresponding European Patent Application: EP 31559FZ900; Date: Dec. 30, 2004.

"PCR Detection of Bacteria in Seven Mnutes"; Authors: Phillip Begrader, et al.; Science magazine, vol. 284, Issue 5413, 449-450, Apr. 16, 1999.

"A Heater-Integrated Transparent Microchannel Chip for Continuous-Flow PCR", Authors: Kai Sun, et al.; Sensors and Actuators B 84 (2002) 283-289; Jan. 9, 2002, pp. 283-289.

"Practical Integration of Polymerase Chain Reaction Amplification and Electrophoretic Analysis in Microfluidic Devices for Genetic Analysis"; Authors: Isabel Rodriguez, et al.; Electrophoresis 2003, 24, pp. 172-178.

"Hepatitis B Viruses with Precore Region Defects Prevail in Persistently Infected Hosts along with Seroconversion to the Antibody against e Atigen"; Authors: Hiroaki Okamoto, et al.; Journal of Virology, vol. 64, No. 3; American Society for Micorbiology' Mar. 1990; pp. 1298-1303.

"Hepatitis B Virus Genotype A Rarely Circulates as an HBe-Minus Mutant: Possible Contribution of a Single Nucleotide in the Precore Region"; Authors: Ji-Su Li, et al.; Journal of Virology, vol. 67, No. 9; American Society for Microbiology; Sep. 1993; pp. 5402-5410.

"Mutation in HBV RNA-Dependent DNA Polymerase Confers Resistance to Lamivudine In Vivo"; Authors: Graham A. Tipples, et al.; American Association for the Study of Liver Diseases, vol. 24, No. 3; pp. 714-717.

Kaneko, S., et al.; "Rapid and Sensitive Method for the Detection of Serum Hepatitis B Virus DNA Using the Polymerase Chain Reaction Technique"; Journal of Clinical Microbiology; vol. 27, No. 9; pp. 1930-1933; Sep. 1989.

Kaneko, S., et al.; "Characterization of primers for optimal amplification of hepatitis B virus DNA in the polymerase chain reaction assay"; Journal of Virological Methods: vol. 29, pp. 225-229; 1990.

Repp, R., et al.; "Genotyping by Multiplexing Polymerase Chain Reaction for Detection of Endemic Hepatitis B Virus Transmission"; Journal of Clinical Microbiology; vol. 31, No. 5; pp. 1095-1102; May 1993.

Balderas-Renteria, I., et al.; "Detection of Hepatitis B Virus in Seropositive and Seronegative Patients with Chronic Liver Disease Using DNA Amplification by PCR"; Archives of Medical Research; vol. 33, pp. 566-571; 2002.

Erhardt, A., et al.; "Quantitative Assay of PCR-Amplified Hepatitis B Virus DNA Using a Peroxidase-Labelled DNA Probe and Enhanced Chemiluminescence"; Journal of Clinical Microbiology; vol. 34, No. 8; pp. 1885-1891; Aug. 1996.

Zhang, M., et al.; "Rapid Detection of Hepatitis B Virus Mutations Using Real-Time PCR and Melting Curve Analysis"; Hepatology; vol. 36; pp. 723-728; 2002.

* cited by examiner

SEQUENCE LISTING

<160> NUMBER OF SEQ ID NOS: 40

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gtggctttgg ggcatggaca tt                                    22

<210> SEQ ID NO 2
<211> LENGTH: 21
<212> TYPE: DNA
<213> ORGANISM: Artificial Sequence

```
<220> FEATURE:
<223> OTHER INFORMATION: primer

<400> SEQUENCE: 2
ctctaaggcc tcccgataca g                                        21

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
tcgaatagaa ggaaagaagt caga                                     24

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gctttggggc atggacattg acc                                      23

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gcttgcctga gtgctgtatg gtga                                     24

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
agcagaggcg gtgtcgagga gat                                      23

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
agagcagagg cggtgtcgag gagat                                    25

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ggctttgggg catggacatt gacc                                     24
```

```
<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
taggacccct gctcgtgtaa                                                    20

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
agaaaattga gagaagtcca cca                                                23

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
tggtggactt ctctcaattt tc                                                 22

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gaagatgagg catagcagca g                                                  21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cgatccatac tgcggaactc                                                    20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gacgggacgt aaacaaagga                                                    20

<210> SEQ ID NO 15
<211> LENGTH: 16
<212> TYPE: DNA
<213> ORGANISM: Artificial Sequence
<220> FEATURE:
<223> OTHER INFORMATION: primer
```

```
<400> SEQUENCE: 15
gaatcccgcg gacgac                                                    16

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gaccgcgtaa agagaggtg                                                 19

<210> SEQ ID NO 17
<211> LENGTH: 16
<212> TYPE: DNA
<213> ORGANISM: Artificial Sequence
<220> FEATURE:
<223> OTHER INFORMATION: primer

<400> SEQUENCE: 17
gcggacgacc cctctc                                                    16

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtgcagaggt gaagcgaagt                                                20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
cacctctctt tacgcggtct                                                20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
cgttcacggt ggtctccat                                                 19

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gaggctgtag gcataaattg g                                              21

<210> SEQ ID NO 22
```

```
<211> LENGTH: 20
<212> TYPE: DNA
<213> ORGANISM: Artificial Sequence
<220> FEATURE:
<223> OTHER INFORMATION: primer

<400> SEQUENCE: 22
cttggaggct tgaacagtgg                                                      20

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
tctttgtatt aggaggctgt aggc                                                 24

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ataagggtca atgtccatgc                                                      20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
taggacccct kcbcgtgtta                                                      20

<210> SEQ ID NO 26
<211> LENGTH: 23
<212> TYPE: DNA
<213> ORGANISM: Artificial Sequence
<220> FEATURE:
<223> OTHER INFORMATION: primer

<400> SEQUENCE: 26
mgaaaattga gagaagtcma ccm                                                  23

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
kggtkgactt ctctcaattt tc                                                   22

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
```

```
gaagatgagg catagmagca g                                          21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
cgatccatac tgyrgaactc                                            20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gayggracgt asacsaagka                                            20

<210> SEQ ID NO 31
<211> LENGTH: 16
<212> TYPE: DNA
<213> ORGANISM: Artificial Sequence
<220> FEATURE:
<223> OTHER INFORMATION: primer

<400> SEQUENCE: 31
gaatcchgcg gacgam                                                16

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gwccgcgtaa agagaggyg                                             19

<210> SEQ ID NO 33
<211> LENGTH: 16
<212> TYPE: DNA
<213> ORGANISM: Artificial Sequence
<220> FEATURE:
<223> OTHER INFORMATION: primer

<400> SEQUENCE: 33
gcggacgamc cbtctb                                                16

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gtgcagaggt gaagsgaagt                                            20

<210> SEQ ID NO 35
<211> LENGTH: 20
<212> TYPE: DNA
```

```
<213> ORGANISM: Artificial Sequence
<220> FEATURE:
<223> OTHER INFORMATION: primer

<400> SEQUENCE: 35
crcctctctt tacgcggwct                                          20

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
cgttcacggt ggtykccat                                           19

<210> SEQ ID NO 37
<211> LENGTH: 16
<212> TYPE: DNA
<213> ORGANISM: Artificial Sequence
<220> FEATURE:
<223> OTHER INFORMATION: primer

<400> SEQUENCE: 37
gaggctgtag gcataa                                              16

<210> SEQ ID NO 38
<211> LENGTH: 18
<212> TYPE: DNA
<213> ORGANISM: Artificial Sequence
<220> FEATURE:
<223> OTHER INFORMATION: primer

<400> SEQUENCE: 38
cttggaggck tgaamagt                                            18

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
tstttgtayt vggaggctgt aggc                                     24

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
atahgkrtca atgtccatgc                                          20
```

PCR PRIMER SET FOR DETECTING HEPATITIS B VIRUS, METHOD FOR DETECTING HEPATITIS B USING THE PRIMER SET, AND HEPATITIS B VIRUS DETECTION KIT INCLUDING THE PRIMER SET

BACKGROUND OF THE INVENTION

This application claims priority from Korean Patent Application No. 2003-56432, filed on Aug. 14, 2003, in the Korean Intellectual Property Office, the disclosure of which is incorporated herein in its entirety by reference.

1. Field of the Invention

The present invention relates to a primer set selected from the group consisting of primers having nucleotide sequences as set forth in SEQ ID NOS: 1 through 40, a method for detecting hepatitis B virus in which PCR is performed using the primer set, and a hepatitis B virus detection kit including the primer set.

2. Description of the Related Art

Hepatitis B is a representative virus infectious disease prevalent worldwide. It is one of common infectious diseases, ranking ninth as a cause of death. More than 300 millions of the global population is chronic hepatitis B virus carriers. Therefore, chronic hepatitis, hepatocirrhosis, liver cancer, and the like cause a million of death per a year. In this country, it is known that about 5-10% of the entire population is hepatitis B virus carriers.

Hepatitis B virus (HBV) is a virus that is consisted of viral proteins including three antigen proteins, HBsAg, HBcAg, and HBeAg. HBV DNA is protected by a protein structure called as core antigen (HBcAg) and a core is enveloped with an envelope protein known as surface antigen or S antigen (HBsAg).

As detection methods for hepatitis B, there have been widely used liver function tests that quantify T protein, albumin, T bilirubin, sGOT, sGPT, r-GPT, or alkaline phosphatase (ALP), serological detection of HBsAg and HBeAg using enzyme immunoassay, and the like. However, these methods are effective in detecting advanced hepatitis B but have problems such as difficulty of early diagnosis and low reliability.

Therefore, recently, there have been widely used a hybrid capture assay, a branched DNA assay, and a genetic assay based on polymerase chain reaction (PCR). In particular, the PCR-based genetic assay is preferred because it has high sensitivity and rapidity, and a pharmacological action against hepatitis B can be understood by observing the degree of proliferation of HBV.

PCR is a technique in which when a primer set binds to complementary strands of target nucleic acid sequence, a gene between the two primer binding sites is amplified to more than several hundreds of thousands of copies within a short time. PCR is well known in the pertinent art. In PCR, two nucleic acid primers complementary to corresponding strands of a target nucleic acid sequence are annealed to denatured strands of the target nucleic acid sequence under hybridization conditions, and then DNA polymerase, which is normally thermal stable, initiates extension at the ends of the hybridized primers to obtain DNA double strands. The above procedure is repeated to multiply the target nucleic acid sequence. When the nucleic acid primers are not hybridized with the target nucleic acid sequence, no amplified PCR products are obtained. In this case, the PCR primers serve as hybridization probes.

The PCR products thus amplified can be detected by observing labeled nucleotides in amplified strands using labeled primers. The labeled primers may be primers labeled with radioactive substance, fluorescent dye, digoxygenin, horseradish peroxidase, alkaline phosphatase, acridium ester, biotin, and jack bean urease, but are not limited thereto. PCR products obtained using non-labeled primers can be detected by visualization with dye after gel electrophoresis.

However, with respect to diagnosis of hepatitis B based on these PCR techniques, there may arise problems in that a long gene amplification time of 2-3 hours is required, false positive or false negative results may be yielded, and accurate diagnosis is difficult due to the presence of different genotypes. Therefore, to increase the diagnostic accuracy for hepatitis B, detection methods using both PCR and hybridization have been suggested. However, these detection methods also require an excessively long detection time and are costly.

SUMMARY OF THE INVENTION

The present invention provides a primer set for detecting hepatitis B virus rapidly and accurately, a method for detecting hepatitis B virus by PCR using the primer set, and a hepatitis B virus detection kit including the primer set.

According to an aspect of the present invention, there is provided a PCR set selected from the group consisting of the following primer sets: (a) a primer set including a primer having a nucleotide sequence as set forth in SEQ ID NO:1 and a primer having a nucleotide sequence as set forth in SEQ ID NO:2; (b) a primer set including the primer having the nucleotide sequence as set forth in SEQ ID NO:1 and a primer having a nucleotide sequence as set forth in SEQ ID NO:3; (c) a primer set including a primer having a nucleotide sequence as set forth in SEQ ID NO:4 and a primer having a nucleotide sequence as set forth in SEQ ID NO:5; (d) a primer set including the primer having the nucleotide sequence as set forth in SEQ ID NO:4 and a primer having a nucleotide sequence as set forth in SEQ ID NO:6; (e) a primer set including the primer having the nucleotide sequence as set forth in SEQ ID NO:4 and a primer having a nucleotide sequence as set forth in SEQ ID NO:7; (f) a primer set including a primer having a nucleotide sequence as set forth in SEQ ID NO:8 and the primer having the nucleotide sequence as set forth in SEQ ID NO:7; (g) a primer set including a primer having a nucleotide sequence as set forth in SEQ ID NO:9 and a primer having a nucleotide sequence as set forth in SEQ ID NO:10; (h) a primer set including a primer having a nucleotide sequence as set forth in SEQ ID NO:11 and a primer having a nucleotide sequence as set forth in SEQ ID NO:12; (i) a primer set including a primer having a nucleotide sequence as set forth in SEQ ID NO:13 and a primer having a nucleotide sequence as set forth in SEQ ID NO:14; (j) a primer set including a primer having a nucleotide sequence as set forth in SEQ ID NO:15 and a primer having a nucleotide sequence as set forth in SEQ ID NO:16; (k) a primer set including a primer having a nucleotide sequence as set forth in SEQ ID NO:17 and a primer having a nucleotide sequence as set forth in SEQ ID NO:18; (l) a primer set including a primer having a nucleotide sequence as set forth in SEQ ID NO:19 and a primer having a nucleotide sequence as set forth in SEQ ID NO:20; (m) a primer set including a primer having a nucleotide sequence as set forth in SEQ ID NO:21 and a primer having a nucleotide sequence as set forth in SEQ ID NO:22; (n) a primer set including a primer having a nucleotide sequence as set forth in SEQ ID NO:23 and a primer having a nucleotide sequence as set forth in SEQ ID NO:24; (o) a primer set including a primer having a nucleotide sequence as set forth in SEQ ID-NO:25 and a primer having a nucleotide sequence as set forth in SEQ ID NO:26; (p) a primer set including a primer having a nucleotide sequence as set forth in SEQ ID NO:27 and a primer having a nucleotide sequence as set forth in SEQ ID NO:28; (q) a primer set including a primer having a nucleotide sequence as set forth in SEQ ID NO:29 and a primer having a nucleotide sequence as set forth in SEQ ID NO:30; (r) a primer set including a primer having a nucleotide sequence as set forth in SEQ ID NO:31 and a primer having a nucleotide sequence as set forth in SEQ ID NO:32; (s) a primer set including a primer having a nucleotide sequence as set forth in SEQ ID NO:33 and a primer having a nucleotide sequence as set forth in SEQ ID NO:34; (t) a primer set including a primer having a nucleotide sequence as set forth in SEQ ID NO:35 and a primer having a nucleotide sequence as set forth in SEQ ID NO:36; (u) a primer set including a primer having a nucleotide sequence as set forth in SEQ ID NO:37 and a primer having a nucleotide sequence as set forth in SEQ ID NO:38; and (v) a primer set including a primer having a nucleotide sequence as set forth in SEQ ID NO:39 and a primer having a nucleotide sequence as set forth in SEQ ID NO:40.

According to another aspect of the present invention, there is provided a method for detecting hepatitis B virus, which includes amplifying a nucleic acid sample obtained from an organism by PCR using the primer set.

According to another aspect of the present invention, there is provided a hepatitis B virus detection kit including the primer set.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
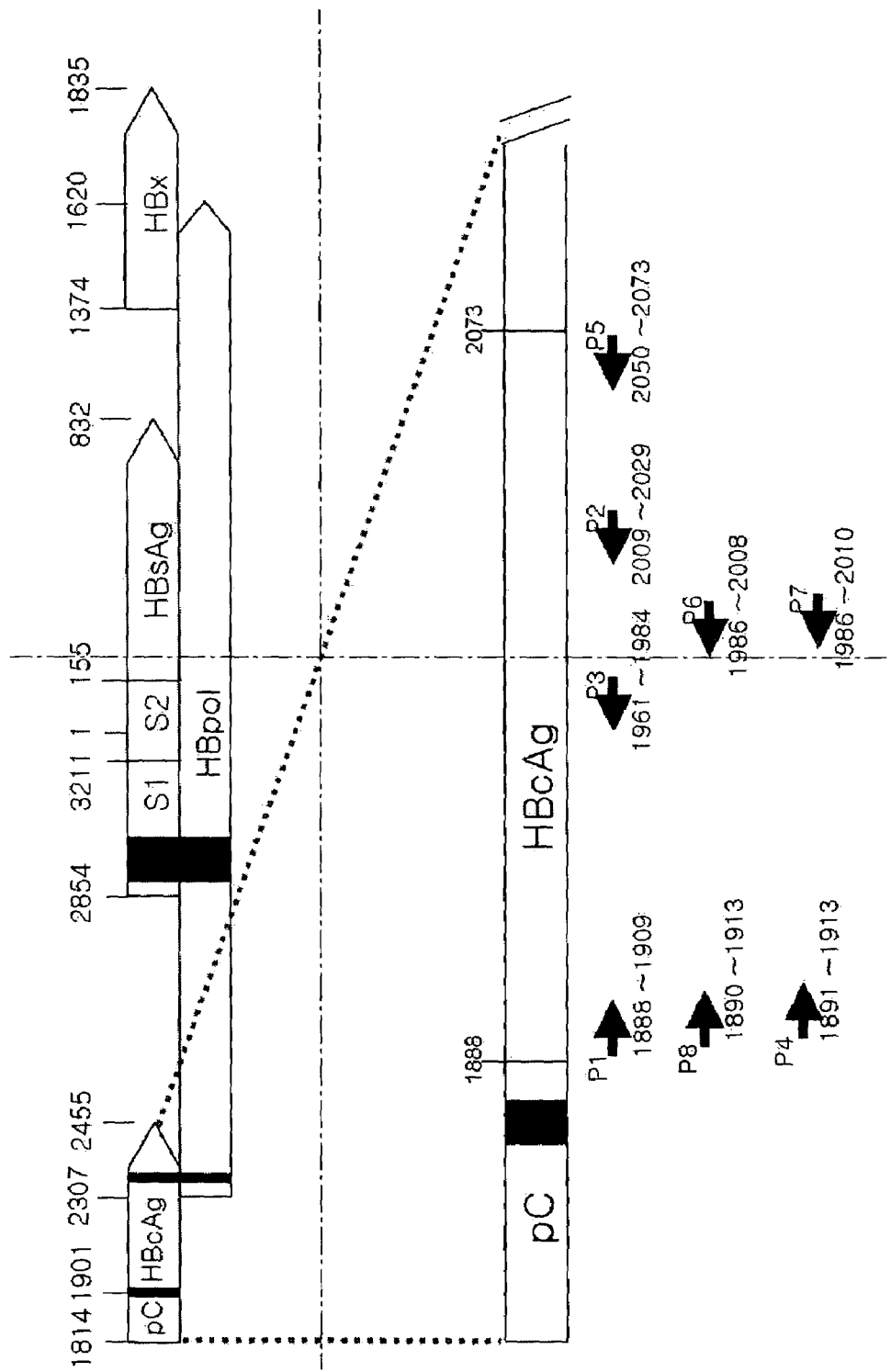
FIG. 1 schematically illustrates the genome sequence of hepatitis B virus (HBV) including target nucleotide sequences for PCR primer sets according to the present invention and the positions of the HBV genome sequence binding with primers of SEQ ID NOS: 1 through 8 according to the present invention.

The present invention provides a PCR set selected from the group consisting of the following primer sets: (a) a primer set including a primer having a nucleotide sequence as set forth in SEQ ID NO:1 and a primer having a nucleotide sequence as set forth in SEQ ID NO:2; (b) a primer set including the primer having the nucleotide sequence as set forth in SEQ ID NO:1 and a primer having a nucleotide sequence as set forth in SEQ ID NO:3; (c) a primer set including a primer having a nucleotide sequence as set forth in SEQ ID NO:4 and a primer having a nucleotide sequence as set forth in SEQ ID NO:5; (d) a primer set including the primer having the nucleotide sequence as set forth in SEQ ID NO:4 and a primer having a nucleotide sequence as set forth in SEQ ID NO:6; (e) a primer set including the primer having the nucleotide sequence as set forth in SEQ ID NO:4 and a primer having a nucleotide sequence as set forth in SEQ ID NO:7; (f) a primer set including a primer having a nucleotide sequence as set forth in SEQ ID NO:8 and the primer having the nucleotide sequence as set forth in SEQ ID NO:7; (g) a primer set including a primer having a nucleotide sequence as set forth in SEQ ID NO:9 and a primer having a nucleotide sequence as set forth in SEQ ID NO:10; (h) a primer set including a primer having a nucleotide sequence as set forth in SEQ ID NO:11 and a primer having a nucleotide sequence as set forth in SEQ ID NO:12; (i) a primer set including a primer having a nucleotide sequence as set forth in SEQ ID NO:13 and a primer having a nucleotide sequence as set forth in SEQ ID NO:14; (j) a primer set including a primer having a nucleotide sequence as set forth in SEQ ID NO:15 and a primer having a nucleotide sequence as set forth in SEQ ID NO:16; (k) a primer set including a primer having a nucleotide sequence as set forth in SEQ ID NO:17 and a primer having a nucleotide sequence as set forth in SEQ ID NO:18; (l) a primer set including a primer having a nucleotide sequence as set forth in SEQ ID NO:19 and a primer having a nucleotide sequence as set forth in SEQ ID NO:20; (m) a primer set including a primer having a nucleotide sequence as set forth in SEQ ID NO:21 and a primer having a nucleotide sequence as set forth in SEQ ID NO:22; (n) a primer set including a primer having a nucleotide sequence as set forth in SEQ ID NO:23 and a primer having a nucleotide sequence as set forth in SEQ ID NO:24; (o) a primer set including a primer having a nucleotide sequence as set forth in SEQ ID NO:25 and a primer having a nucleotide sequence as set forth in SEQ ID NO:26; (p) a primer set including a primer having a nucleotide sequence as set forth in SEQ ID NO:27 and a primer having a nucleotide sequence as set forth in SEQ ID NO:28; (q) a primer set including a primer having a nucleotide sequence as set forth in SEQ ID NO:29 and a primer having a nucleotide sequence as set forth in SEQ ID NO:30; (r) a primer set including a primer having a nucleotide sequence as set forth in SEQ ID NO:31 and a primer having a nucleotide sequence as set forth in SEQ ID NO:32; (s) a primer set including a primer having a nucleotide sequence as set forth in SEQ ID NO:33 and a primer having a nucleotide sequence as set forth in SEQ ID NO:34; (t) a primer set including a primer having a nucleotide sequence as set forth in SEQ ID NO:35 and a primer having a nucleotide sequence as set forth in SEQ ID NO:36; (u) a primer set including a primer having a nucleotide sequence as set forth in SEQ ID NO:37 and a primer having a nucleotide sequence as set forth in SEQ ID NO:38; and (v) a primer set including a primer having a nucleotide sequence as set forth in SEQ ID NO:39 and a primer having a nucleotide sequence as set forth in SEQ ID NO:40.

The present invention also provides a method for detecting hepatitis B virus, which includes amplifying a nucleic acid sample obtained from an organism by PCR using the primer set.

The PCR may be a two-step PCR including a denaturation step and an annealing and extension step and may be performed for 30 minutes or less.

The PCR may be performed on a micro PCR chip using 0.2-1 µM of each primer and 0.01 pg to 1 µg of a template DNA.

The micro PCR chip may include a silicon wafer, a surface of which is formed

The PCR may be performed under conditions of denaturation at 86-97° C. for 1-30 seconds and annealing and extension at 60-70° C. for 6-30 seconds with a PCR chamber made by silicon lithography and the other surface is formed with a heater for heating the PCR chamber; and a glass wafer having an inlet and an outlet.

The present invention also provides a hepatitis B virus detection kit including the primer set.

To facilitate understanding of the invention, a number of terms are defined below. The term "nucleic acid" refers to a molecule in which the 3'-end of pentose in one nucleotide is linked to the 5'-end of adjacent pentose via phosphodiester bond and nucleotide residues are presented as a specific sequence, i.e., linear sequence.

The term "target nucleic acid" or "nucleic acid target" refers to a specific nucleic acid sequence of interest. Therefore, "target" may be present in another nucleic acid molecule or large nucleic acid molecule. As used herein, preferably, the term "target" refers to a sequence of two or more nucleotides in a gene of hepatitis B virus (HBV).

The term "nucleic acid primer" refers to an oligonucleotide or polynucleotide used in a method of the present invention. The oligonucleotide may also be used as an amplification primer for PCR. However, as used herein, the amplification primer is called as simply "primer". Here, the oligonucleotide or polynucleotide may include a modified bond such as phosphorothioate bond.

A target DNA for the PCR primer sets according to the present invention is a genetic fragment that contains few genetic variations in the core of HBV. Therefore, diagnostic accuracy is excellent and diagnosis for different genotypes such as genotypes A, B, C, D, E, and F is possible. In addition, accuracy and reproducibility of diagnosis are excellent in a rapid PCR machine that takes 30 minutes or less as well as in a PCR machine that takes generally 2-3 hours.

FIG. 1 schematically illustrates a genome sequence of HBV including target nucleotide sequences for PCR primer sets according to the present invention and the positions of the HBV genome sequence binding with primers of SEQ ID NOS: 1 through 8 according to the present invention. Although not shown, primers of SEQ ID NOS: 9-12 and 23-26 are attached to a surface gene region of HBV gene and primers of SEQ ID NOS: 13-22 and 27-36 are attached to an x gene region of the HBV gene.

Figure 2:
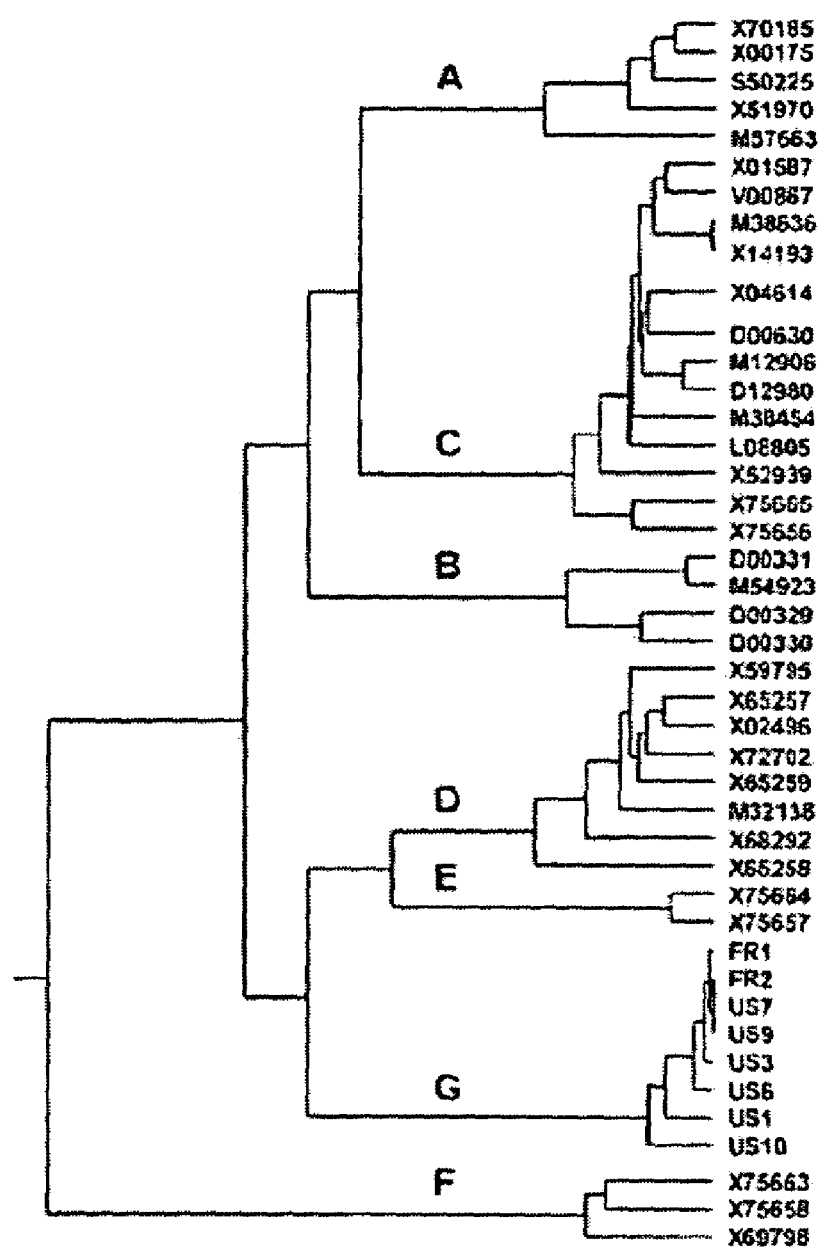
FIG. 2 illustrates a branch diagram of genotypes A-F of HBV and 90% or more homology regions of each genotype selected as candidate regions for primers to design PCR primer sets according to the present invention.

FIG. 2 illustrates a branch diagram of genotypes A-F of HBV that can be detected using the PCR primer sets according to the present invention. Such a branch diagram of genotypes is a diagram that represents genomic groups having a high sequence homology to each other and genomes of each genomic group having commonly a specific gene region absent from other genomic groups.

Hereinafter, the present invention will be described more specifically by Examples. However, the following Examples are provided only for illustrations and thus the present invention is not limited to or by them.

EXAMPLE 1

Preparation of Primers

Primers are required to be designed so that they amplify a HBV gene containing various mutant sequences and distinguishes the HBV gene from another virus gene. For this, the present inventors (1) investigated and analyzed the characteristics of HBV genome, (2) selected the regions of the HBV genome that are genetically well conserved and have few variations by environmental factors and the like as candidate regions for primers, and (3) designed primers based on the selected regions of the HBV genome.

1.1 Characterization of HBV Genome

Referring to FIG. 1, a HBV genome is a 3.2 kb in size and contains four genes, S, C, P, and X.

HBsAg encoded by the S gene has serological antigenic sites for determining serological subtypes. That is, HBsAg carries a common determinant "a" (amino acid residue: 124-147) and subtype specific determinants, "dw, dr, yw, and yr" (amino acid 122 (d=lysine and y=arginine) and amino acid 160 (w=lysine and r=arginine) for immune response against monoclonal antibody. The common determinant "a" for all subtypes of HBsAg is a main region for anti-HBs immune response and is present in the form of various mutations in HBV. In classification of genotypes of HBV, complete viral genomes are compared (8% for genotypes A-D, 14% for genotype F). The nucleotide sequence of the S gene is utilized as a standard in classifying as a new genotype [Magnius LO et al., Intervirology, 1995; 38(1-2): 24-34].

HBeAg and HBcAg encoded by the C gene have clinically important genetic polymorphisms. HBeAg is an important protein marker of HBV to be recognized by the immune system of a host cell and has genetic polymorphisms to avoid a host cell-mediated immune response. In particular, a preCore mutation that causes premature termination of preCore (called as "translation stop codon mutation") has been well known [Li J S et al, J. Virol. 1993 September; 67(9): 5402-10 and Okamoto H. et al., J. Virol. 1990 March; 64(3): 1298-303].

HBV polymerase encoded by the P gene has reverse-transcription activity. The reverse-transcription activity is inhibited by lamivudine which is a nucleoside analog and is also used for the treatment of HIV infection. It is known that long-term drug administration induces selective mutation of a YMDD motif related to the reverse-transcription activity [Tipples G A. et al., Hepatology, 1996, September; 24(3): 714-7].

As described above, after investigating the mutation and genotypes of known HBV genome, well-conserved gene regions were selected as candidate regions for primers.

1.2 Selection of Candidate Regions for Primers

Currently known gene groups of the genotypes A-F of HBV were searched in GenBank and patent documents. The homology and mutation sites of the nucleotide sequences of these gene groups were analyzed and regions having a 90% or more homology for each genotype were selected as candidate regions for primers.

FIG. 2 illustrates a branch diagram of the genotypes A-F of HBV and selection of 90% or more homology regions for each genotype as candidate regions for primers to design PCR primer sets according to the present invention.

1.3 Design of Primers i) Requirements of Primers for Rapid PCR

Various requirements must be satisfied to design primers for rapid PCR. PCR is based on effective variation of temperature for maximizing enzyme activity. That is, temperature and enzyme activity are main factors for PCR. In a conventional PCR, three-steps, i.e., denaturation, annealing, and extension are performed by changing the temperature.

In the present invention, to minimize a time required for polymerization by polymerase, classical annealing and extension steps were performed at the same time. Furthermore, to maintain a high polymerization yield, primers with high melting temperature (Tm) were used.

Therefore, primers of the present invention were designed so that PCR products had at least a difference of 100-200 bps. In addition, primers of the present invention were designed to satisfy the following requirements: amplification of only a specific region, creation of sufficient PCR products so that the PCR products can be used in next analysis step, no interference between the primers during PCR, high Tm, no hairpin structures, no primer self-dimers or primer pair-dimers, no more than 4 consecutive repeats of one base, no microsatellites, and no repetitive sequences. Primers were designed by HYBsimulator™ (Advanced Gene Computing Technologies, Inc.).

ii) Selection of Primers

Detailed sequences of the designed primers were analyzed using ClustalX software based on a 90% homology of the candidate regions for the primers.

Primers with 100% homology to the candidate regions (for example, primer 13) were selected as desired primers. On the other hand, primers that had no 100% homology to the candidate regions but were used for important amplification sites (for example, primer 14) were designed to contain degenerate bases instead of bases of nucleotide mismatch sites after sequencing.

TABLE 1

| Degenerate bases | |
|---|---|
| Degenerate Base | Nucleotide |
| R | A/G |
| Y | C/T |
| M | A/C |
| K | G/T |
| S | C/G |
| W | A/T |
| B | C/G/T |
| D | A/G/T |
| H | A/C/T |
| V | A/C/G |
| N | A/C/G/T |

The sequences and characteristics of the designed primers are summarized in Table 2 below.

TABLE 2

Sequences and characteristics of primers

| Primer Set No. | Primer No. | Sequence (5'→3') | Primer Length (bp) | Primer Tm(° C.) | Primer Direction | PCR product Length (bp) |
|---|---|---|---|---|---|---|
| GS01 | P1 | GTGGCTTTGGGGCATGGACATT | 22 | 61.5 | F | 142 |
| | P2 | CTCTAAGGCCTCCCGATACAG | 21 | 52.4 | R | |
| GS02 | P1 | GTGGCTTTGGGGCATGGACATT | 22 | 61.5 | F | 97 |
| | P3 | TCGAATAGAAGGAAAGAAGTCAGA | 24 | 51.3 | R | |
| GS03 | P4 | GCTTTGGGGCATGGACATTGACC | 23 | 63.1 | F | 183 |
| | P5 | GCTTGCCTGAGTGCTGTATGGTGA | 24 | 60.1 | R | |
| GS04 | P4 | GCTTTGGGGCATGGACATTGACC | 23 | 63.1 | F | 118 |
| | P6 | AGCAGAGGCGGTGTCGAGGAGAT | 23 | 62.2 | R | |
| GS05 | P4 | GCTTTGGGGCATGGACATTGACC | 23 | 63.1 | F | 120 |
| | P7 | AGAGCAGAGGCGGTGTCGAGGAGAT | 25 | 64.3 | R | |

TABLE 2-continued

Sequences and characteristics of primers

| Primer Set No. | Primer No. | Primer Sequence (5'→3') | Primer Length (bp) | Primer Tm(° C.) | Primer Direction | PCR product Length (bp) |
|---|---|---|---|---|---|---|
| GS06 | P8 | GGCTTTGGGGCATGGACATTGACC | 24 | 65.8 | F | 121 |
|  | P7 | AGAGCAGAGGCGGTGTCGAGGAGAT | 25 | 64.3 | R |  |
| GS07 | P9 | TAGGACCCCTGCTCGTGTAA | 20 | 60.65 | F | 100 |
|  | P10 | AGAAAATTGAGAGAAGTCCACCA | 23 | 59.26 | R |  |
| GS08 | P11 | TGGTGGACTTCTCTCAATTTTC | 22 | 58.29 | F | 176 |
|  | P12 | GAAGATGAGGCATAGCAGCAG | 21 | 60.13 | R |  |
| GS09 | P13 | CGATCCATACTGCGGAACTC | 20 | 60.62 | F | 175 |
|  | P14 | GACGGGACGTAAACAAAGGA | 20 | 59.97 | R |  |
| GS10 | P15 | GAATCCCGCGGACGAC | 16 | 61.21 | F | 103 |
|  | P16 | GACCGCGTAAAGAGAGGTG | 19 | 58.46 | R |  |
| GS11 | P17 | GCGGACGACCCCTCTC | 16 | 60.31 | F | 153 |
|  | P18 | GTGCAGAGGTGAAGCGAAGT | 20 | 60.6 | R |  |
| GS12 | P19 | CACCTCTCTTTACGCGGTCT | 20 | 59.5 | F | 100 |
|  | P20 | CGTTCACGGTGGTCTCCAT | 19 | 61.99 | R |  |
| GS13 | P21 | GAGGCTGTAGGCATAAATTGG | 21 | 58.73 | F | 100 |
|  | P22 | CTTGGAGGCTTGAACAGTGG | 20 | 60.82 | R |  |
| GS14 | P23 | TCTTTGTATTAGGAGGCTGTAGGC | 24 | 60.16 | F | 154 |
|  | P24 | ATAAGGGTCAATGTCCATGC | 20 | 57.33 | R |  |
| GS15 | P25 | TAGGACCCCTKCBCGTGTTA | 20 |  | F | 100 |
|  | P26 | MGAAAATTGAGAGAAGTCMACCM | 23 |  | R |  |
| GS16 | P27 | KGGTKGACTTCTCTCAATTTTC | 22 |  | F | 176 |
|  | P28 | GAAGATGAGGCATAGMAGCAG | 21 |  | R |  |
| GS17 | P29 | CGATCCATACTGYRGAACTC | 20 |  | F | 175 |
|  | P30 | GAYGGRACGTASACSAAGKA | 20 |  | R |  |
| GS18 | P31 | GAATCCHGCGGACGAM | 16 |  | F | 103 |
|  | P32 | GWCCGCGTAAAGAGAGGYG | 19 |  | R |  |
| GS19 | P33 | GCGGACGAMCCBTCTB | 16 |  | F | 153 |
|  | P34 | GTGCAGAGGTGAAGSGAAGT | 20 |  | R |  |
| GS20 | P35 | CRCCTCTCTTTACGCGGWCT | 20 |  | F | 100 |
|  | P36 | CGTTCACGGTGGTYKCCAT | 19 |  | R |  |
| GS21 | P37 | GAGGCTGTAGGCATAA | 21 |  | F | 100 |
|  | P38 | CTTGGAGGCKTGAAMAGT | 20 |  | R |  |
| GS22 | P39 | TSTTTGTAYTVGGAGGCTGTAGGC | 24 |  | F | 154 |
|  | P40 | ATAHGKRTCAATGTCCATGC | 20 |  | R |  |

F: forward direction, R: reverse direction

EXAMPLE 2

PCR Experiments

To minimize a difference between PCR experiments, other reagents except DNA samples were first mixed to prepare a two-fold concentrated master mixture. Then, the master mixture was mixed with the DNA samples (1:1, by volume) to obtain a PCR mixture.

The composition of the master mixture is as follows:

| | |
|---|---|
| 5xPCR buffer solution | 1.0 µl |
| Distilled water | 1.04 µl |
| 10 mM dNTPs | 0.1 µl |
| 20 µM of each primer mixture | 0.2 µl |
| Enzyme mixture | 0.16 µl |

2.1: PCR on Conventional PCR Tubes

The PCR mixture prepared previously was loaded in MJRsearch PTC-100 machine and a PCR cycle of 95° C. for 20 seconds, 58° C. for 30 seconds, and 72° C. for 40 seconds was then repeated for 40 times.

Figure 3:
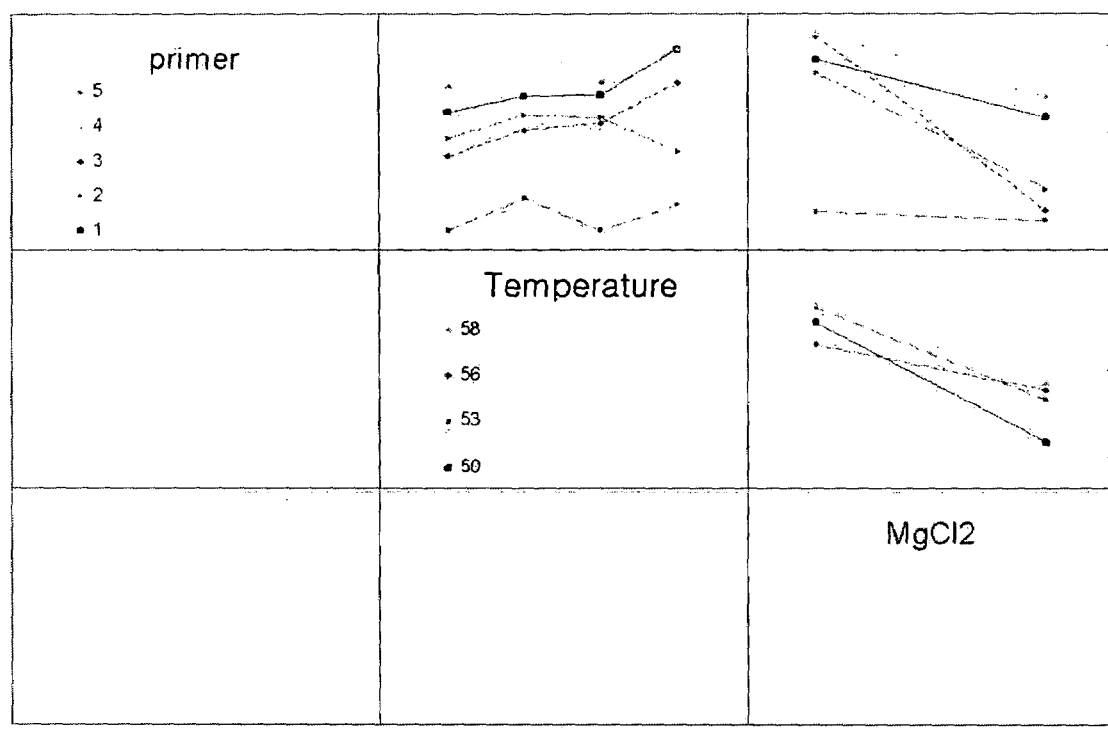
FIG. 3 illustrates Interaction Plot-Data Means for Concentration for each primer according to the present invention after 40 cycles of PCR at 95° C. for 20 seconds, 58° C. for 30 seconds, and 72° C. for 40 seconds, using MJResearch PTC-100 machine.

To select optimal primers, PCR was performed with varying the type of primers (primers 1-5), experimental temperature (50° C., 53° C., 56° C., and 59° C.), and the concentration of MgCl$_2$ (2.5 mM and 3.5 mM), and correlation between these experimental parameters is shown in FIG. 3.

FIG. 3 illustrates Interaction Plot-Data Means for Concentration for each primer. According to the experimental result, as compared to the primer 5 used as control (represented by red line), performance difference between other primers was insignificant.

2.2 Rapid PCR Experiments

Figure 4A:
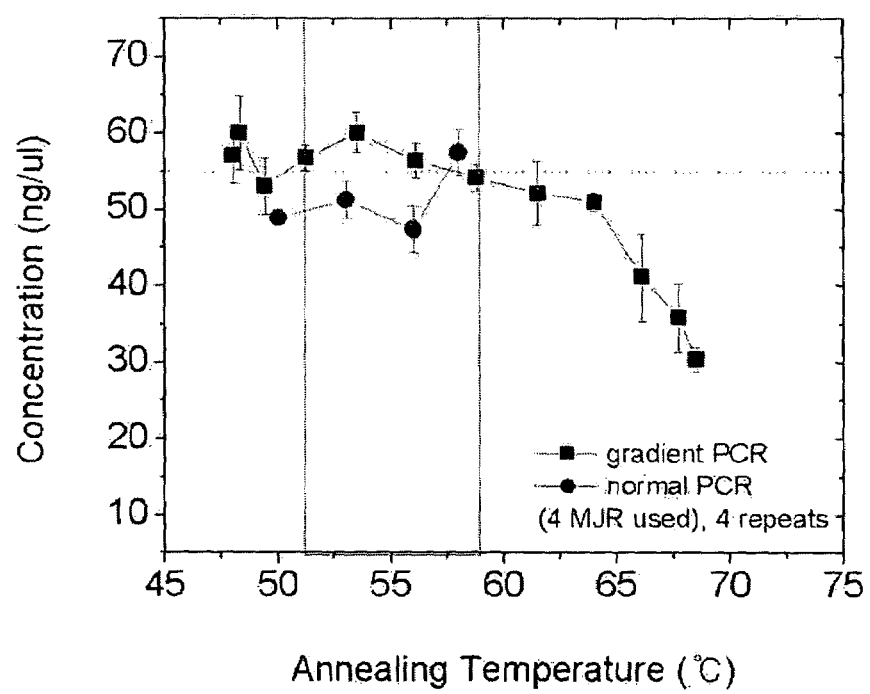
FIGS. 4A and 4B are graphs that illustrate respectively the concentration of PCR products versus annealing temperature and the concentration of PCR products versus extension temperature, in a two-step PCR analysis using primers of the present invention.
Figure 4B:
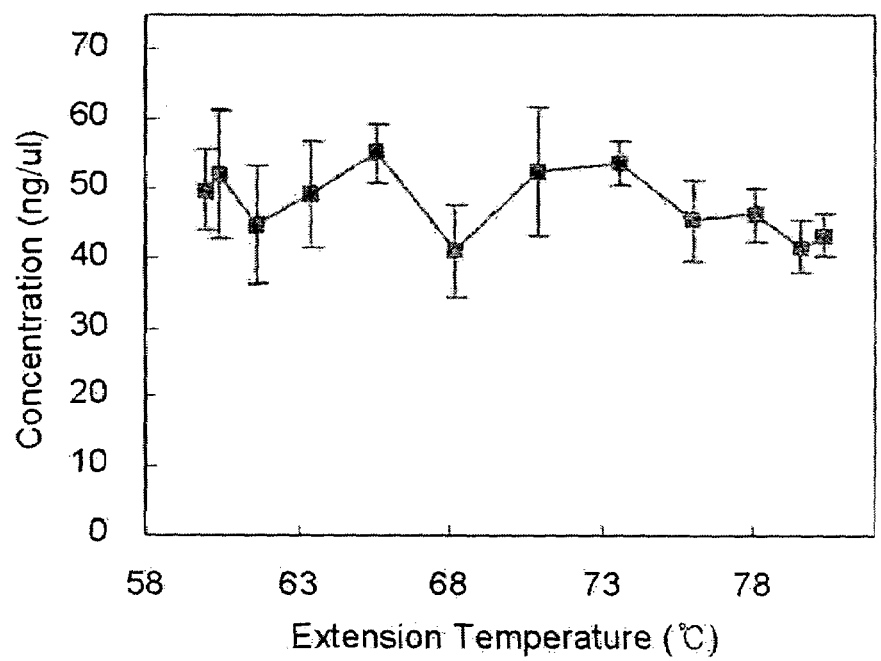

The performance of the above PCR mixture at annealing and extension temperatures was analyzed and two-step temperature experiments for obtaining optimal PCR time were performed. The experimental results are presented in FIGS. 4A and 4B. As shown in FIGS. 4A and 4B, the primers of the present invention exhibited high amplification efficiency even at a high annealing temperature due to high Tm. The result shows that the annealing temperatures are within the extension temperature range.

Figure 4C:
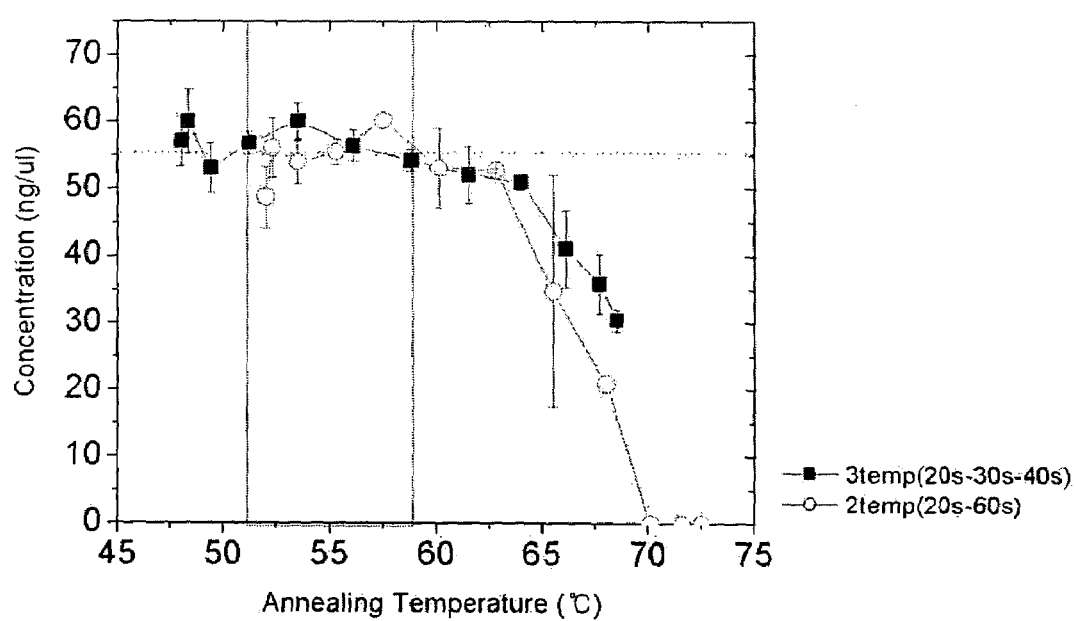
FIG. 4C is a comparative graph that illustrates the concentration of PCR products versus annealing temperature in a typical three-step PCR analysis and a two-step PCR analysis using primers of the present invention.

Based on the above result, comparative experiments between a three-step PCR (95° C. for 20 seconds, 58° C. for 30 seconds, and 72° C. for 40 seconds) and a two-step PCR (95° C. for 20 seconds and 68° C. for 30 seconds) were performed to obtain an optimal time required for PCR and the results are shown in FIG. 4C. As shown in FIG. 4C, the two-step PCR exhibited the same pattern for the concentration of PCR products as the three-step PCR.

FIG. 4A illustrates the concentration of PCR products versus annealing temperature and FIG. 4B illustrates the concentration of PCR products versus extension temperature.

2.3 Cross Reactivity Among Viruses

Whether the primers of the present invention react with other viruses was analyzed. First, comparative analysis between known nucleotide sequences was performed using BLAST search. According to the comparative analysis results, the primers of the present invention showed 100% homology with only HBV. When PCR was performed using the following five viruses and human gDNA, no cross reactivity was observed. The experimental results for cross reactivity are summarized in Table 3 below.

TABLE 3

| | Experimental results for cross reactivity | | | | | |
|---|---|---|---|---|---|---|
| Section | HIV | CMV | HPV | HSV-1 | HSV-2 | Human gDNA |
| Number of experiments (n = 9) | — | — | — | — | — | — |
| Sequence matching | NS | NS | NS | NS | NS | NS |

HIV: Human immunodeficiency virus,
CMV: Human cytomegalovirus,
HPV: Human papiloma virus
HSV-1: Human herpes simplex virus type 1,
HSV-2: Human herpes simplex virus type 2
NS: No significant homology

2.4 Analysis of Detection Limit

The detection limit of PCR according to the present invention was analyzed using international standard HBV DNA and the results are summarized in Table 4 below.

DNA samples of the international standard HBV DNA in sera were extracted using Qiagen MinElute kit and purified. To perform PCR, a two-fold concentrated master mixture was prepared and then mixed with the DNA samples (1:1, by volume) to obtain a PCR mixture.

The composition of the master mixture is as follows:

| | |
|---|---|
| 5xPCR buffer solution | 1.0 µl |
| Distilled water | 1.04 µl |
| 10 mM dNTPs | 0.1 µl |
| 20 µM of each primer mixture | 0.2 µl |
| Enzyme mixture | 0.16 µl |

The PCR was performed as the following conditions: 91° C. for 1 second and 63° C. for 15 seconds.

TABLE 4

| | | Micro PCR prohibit analysis | |
|---|---|---|---|
| IU/ml | Positive (%) | 95% detection limit (95% confidence) | 50% detection limit (95% confidence) |
| 100.0 | 100.0 | 18.4 IU/ml | 2.9 IU/ml |
| 50.0 | 100.0 | (13.9-31.0) | (0-6.9) |
| 25.0 | 96.2 | | |
| 15.0 | 100.0 | | |
| 5.0 | 53.8 | | |

2.5 PCR on Microchips

To investigate effects of the primers of the present invention on PCR according to a thermal transfer rate and a temperature gradient between different temperatures, PCR was carried out on micro PCR chips instead of conventional PCR tubes. The micro PCR chips used were made of silicon, and had advantages such as fast thermal transfer in reactants due to several hundreds times faster thermal conductivity than conventional PCR tubes, a fast temperature ramping rate, and maximal thermal transfer due to use of a trace of DNA samples.

Figure 5A:
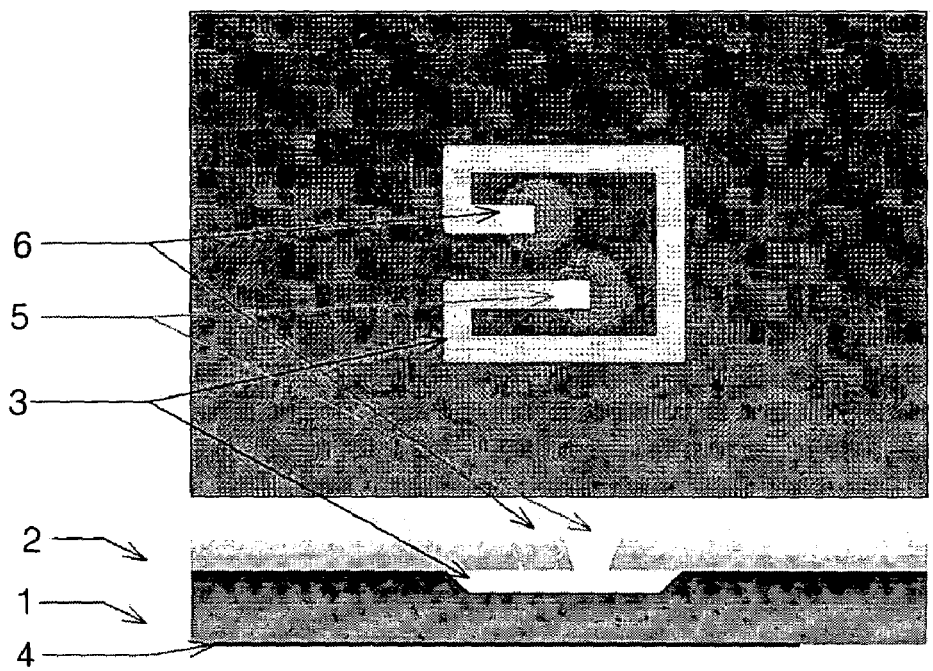
FIG. 5 schematically illustrates a top view and a sectional view (FIG. 5A) and a bottom view (FIG. 5B) of a microchip used in the present invention.
Figure 5B:
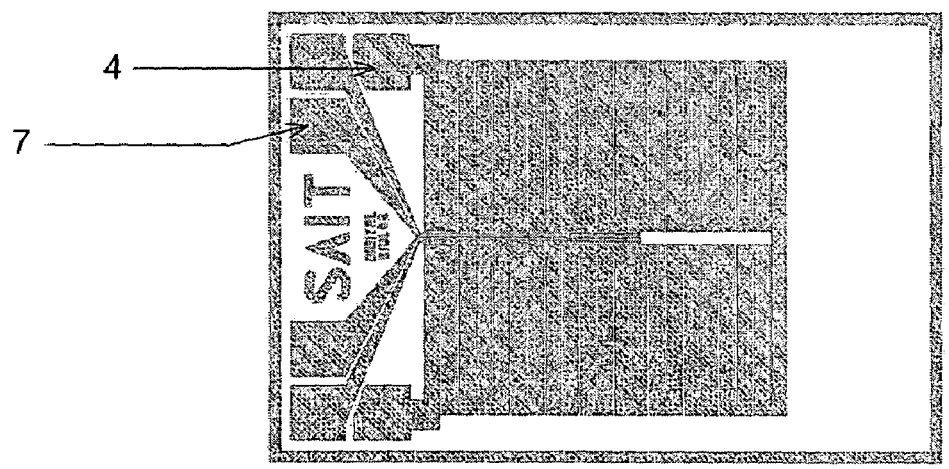

FIG. 5 schematically illustrates a top view and a sectional view (FIG. 5A) and a bottom view (FIG. 5B) of a microchip used in this Example. Referring to FIGS. 5A and 5B, the microchip used in a method of the present invention includes a silicon wafer 1 and a glass wafer 2. A micro-chamber 3 for PCR made by silicon lithography is formed at a surface of the silicon wafer 1 and a micro-heater 4 for heating the micro-chamber 3 is formed at the other surface of the silicon wafer 1. The micro-heater 4 is controlled by a micro temperature sensor 7 to precisely control the PCR. The silicon wafer 1 is covered with the glass wafer 2 having a sample inlet 5 and a sample outlet 6. A sample inserted into the micro-chamber 3 formed at the silicon wafer 1 via the sample inlet 5 was heated by the micro-heater 4 to perform PCR. After the PCR, the sample was discharged out via the sample outlet 6.

To perform PCR on the micro PCR chips, the same PCR mixture as in conventional PCR tubes was prepared. Here, there was used the GS04 primer set of Table 2 which produced smaller-sized PCR products and had a high Tm. 1 µl of the PCR mixture was loaded in each of the micro PCR chips, and a PCR cycle of 91° C. for 1 second and 63° C. for 15 seconds was then repeated for 40 times. The experimental resultants were quantified using Labchip (Agilent) and amplification was identified on a 2% TAE agarose gel.

Figure 6:
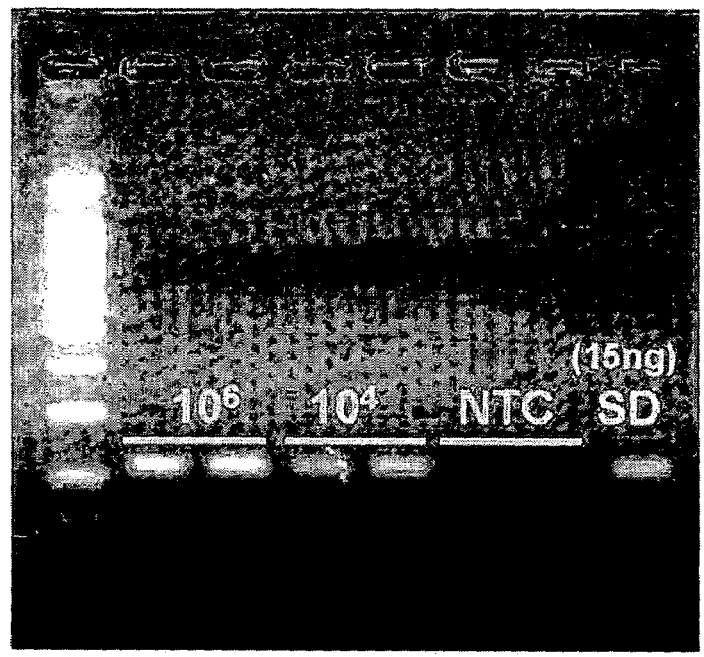
FIG. 6 illustrates results of 2% TAE agarose gel electrophoresis for PCR products after a two-step PCR on a microchip using primers according to the present invention.

FIG. 6 shows electrophoretic results on a 2% TAE agarose gel after the amplification. Here, $10^6$ and $10^4$ indicate the copy numbers of HBV templates, NTC (no template control) is a negative control for PCR, and SD (standard) is a positive control for electrophoresis.

Figure 7A:
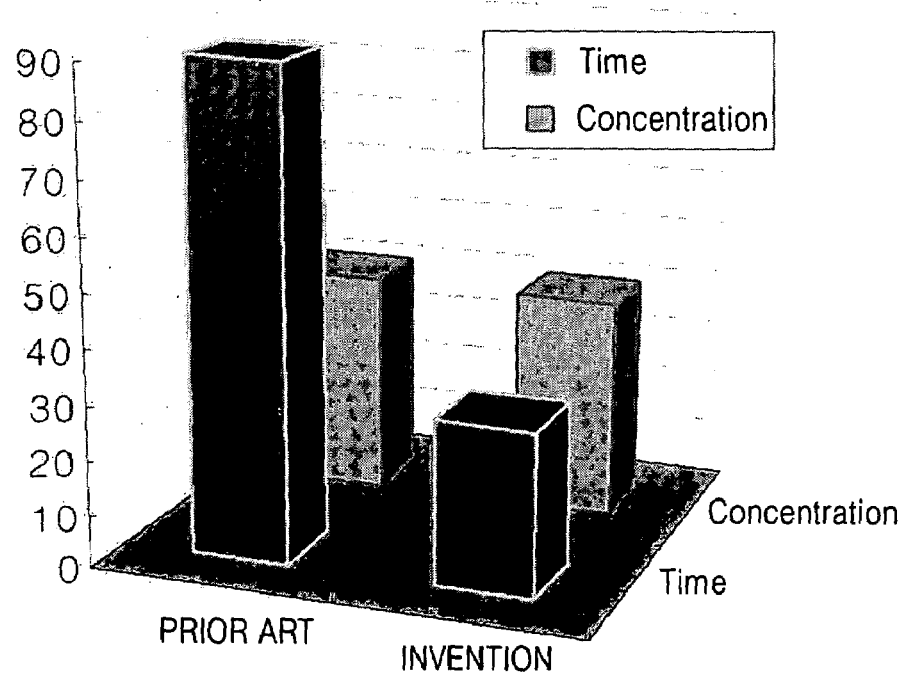
FIG. 7A is a comparative graph that illustrates a PCR time required for almost same DNA concentration in the present invention and a conventional technique.
Figure 7B:
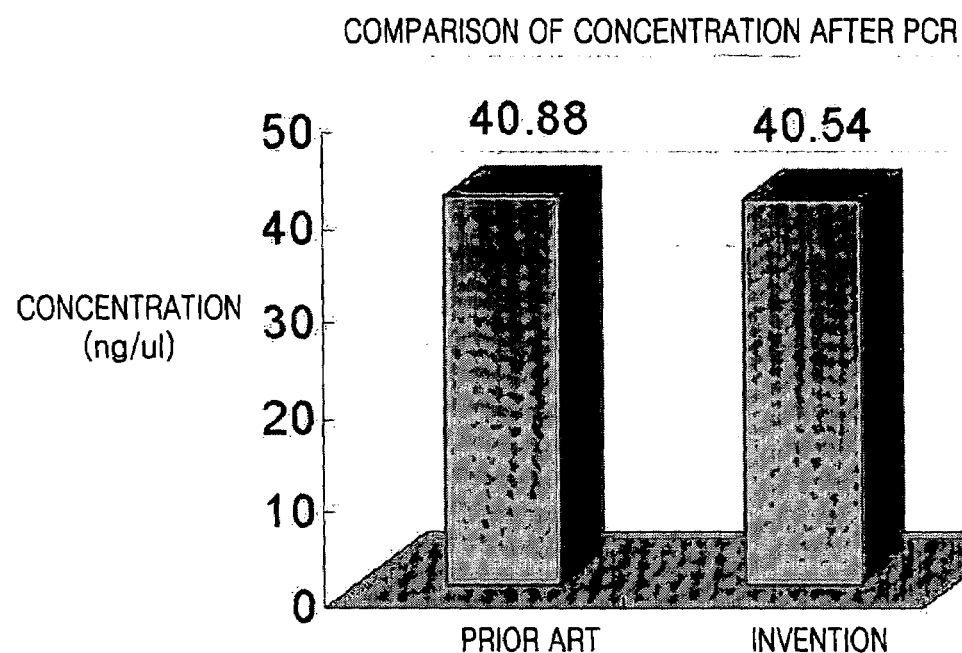
FIG. 7B is an enlarged view that illustrates only the concentration values of FIG. 7A.

FIGS. 7A and 7B are comparative views that illustrate the concentrations of PCR products with respect to the time required for PCR in a micro PCR chip according to the present invention and in a conventional PCR machine. Referring to FIGS. 7A and 7B, a time required for obtaining 40.54 ng/µl of a PCR product on a micro PCR chip according to the present invention was only 28 minutes. This is in contrast to 90 minutes required for obtaining 40.88 ng/µl of a PCR product using a conventional PCR machine. That is, a time required for obtaining a predetermined concentration of a PCR product using the PCR technology of the present invention was only about one-third of a time required for obtaining almost the same concentration of a PCR product using a conventional PCR machine.

2.6 Rapidity and Accuracy

The rapidity and accuracy of a PCR technique of the present invention and conventional PCR kits (Comparative Example 1: Chiron (Procleix Ultrio™) and Comparative Example 2: Roche (AMPLINAT MPX)) were evaluated and the results are presented in Table 5 below.

TABLE 5

| Section | Invention | Comparative Example 1 | Comparative Example 2 |
|---|---|---|---|
| Application | Screening test | Blood screening | Blood screening |
| LOD value | 18.4 IU/mL (95% detection limit) | 6.2 IU/mL | 30 copies/ml |
| Amplification time | 28.3 minutes | ~1 hour | ~2 hours |
| Amplification target | Gene | rRNA | Gene (amplification and hybridization) |

LOD: Limit of detection
IU (International Unit) = 3-7 copies

2.7 Reproducibility

Reproducibility of the PCR technique according to the present invention was evaluated with respect to days and workers and the results are presented in Tables 6 and 7.

TABLE 6

Reproducibility with respect to days (HBV templates = $10^6$ copies/µl)

| Section | 1 day | 2 days | 3 days | 4 days | 5 days |
|---|---|---|---|---|---|
| Number of copies | 3 | 3 | 3 | 3 | 3 |
| Mean (ng/µl) | 44.1 | 41.2 | 49.7 | 47.9 | 45.7 |
| Standard variation | 6.7 | 1.5 | 2.5 | 1.9 | 4.7 |
| Dispersion (%) | 15.1 | 3.8 | 5.1 | 4.0 | 10.3 |

TABLE 7

Reproducibility with respect to workers (HBV templates = $10^6$ copies/µl)

| Section | 1 day | 2 days | 3 days | 4 days | 5 days |
|---|---|---|---|---|---|
| Number of copies | 3 | 3 | 3 | 3 | 3 |
| Mean (ng/µl) | 55.0 | 38.6 | 44.1 | 39.1 | 24.5 |
| Standard variation | 11.5 | 6.4 | 6.7 | 5.8 | 2.0 |
| Dispersion (%) | 20.9 | 16.6 | 15.1 | 14.8 | 8.3 |

In addition, reproducibility of PCR techniques according to the present invention and Comparative Example 1 was evaluated with respect to days and workers and the results are presented in Table 8 below.

TABLE 8

| Section | Invention | Comparative Example 1 |
|---|---|---|
| Reproducibility based on days | (Maximum 15%, mean 8%) HBV $10^6$ copies | (Maximum 44%, mean 27%) HBV $10^{3-6}$ copies |
| Reproducibility based on workers | (Maximum 21%, mean 15%) HBV $10^6$ copies | (Maximum 35%, mean 21%) HBV $10^{4-6}$ copies |

2.8 Specificity

Hepatitis diagnosis was performed for 100 Korean persons using hepatitis detection kits according to the present invention and a conventional technique (Comparative Example 3: Solgent™, a clinical diagnostic kit commercially available in the country) and the results are shown in FIG. 8.

Figure 8:
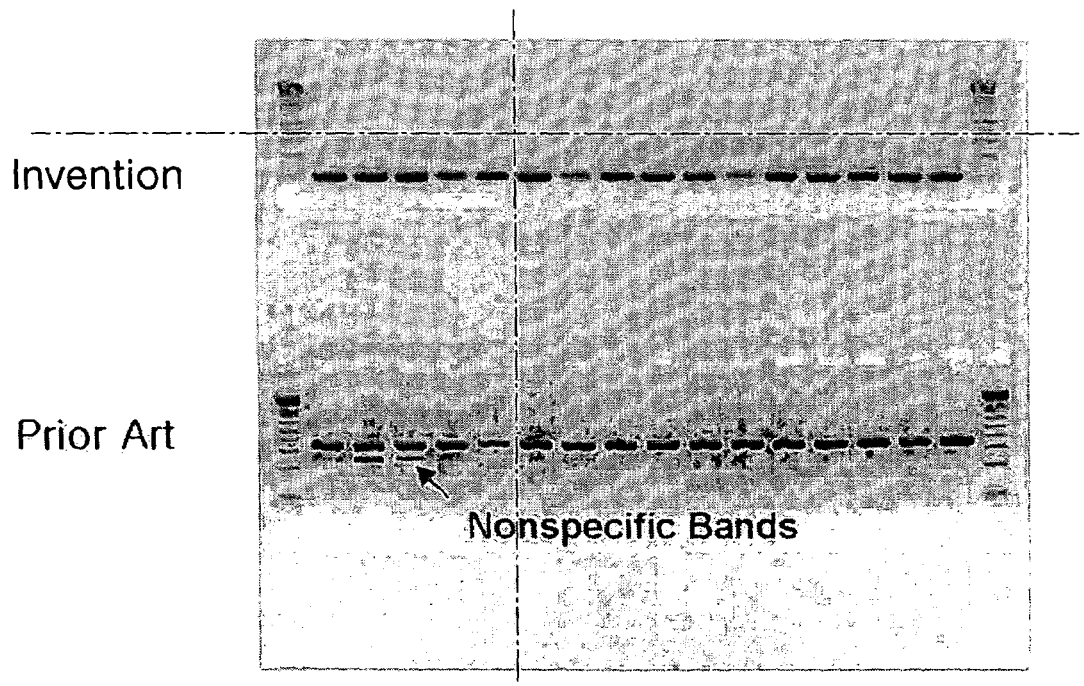
FIG. 8 illustrates diagnostic results for 100 Korean persons based on molecular weight marker after electrophoresis using hepatitis detection kits according to the present invention and a conventional technique.

Referring to FIG. 8, in connection with the hepatitis detection kit according to the conventional technique, bands exhibiting nonspecific reactivity were observed. On the other hand, in the hepatitis detection kit of the present invention, no bands exhibiting nonspecific reactivity were observed.

EXAMPLE 3

Clinical Test

Test subjects were classified into a patient group representing positive reactivity to HBsAg and HBV DNA (Digene) and a normal group representing negative reactivity to HBsAg and HBeAg. Clinical tests were performed in 118 subjects for the patient group and 61 subjects for the normal groups and the test results are presented in Table 9 below.

DNA samples were extracted from the sera of the subjects using Qiagen MinElute kit and purified. To perform PCR, a two-fold concentrated master mixture was prepared and then mixed with the DNA samples (1:1, by volume) to obtain a PCR mixture.

The composition of the master mixture is as follows:

| | |
|---|---|
| 5xPCR buffer solution | 1.0 µl |
| Distilled water | 1.04 µl |
| 10 mM dNTPs | 0.1 µl |
| 20 µM of each primer mixture | 0.2 µl |
| Enzyme mixture | 0.16 µl |

The PCR was performed as the following conditions: 91° C. for 1 second and 63° C. for 15 seconds.

TABLE 9

| | Results of clinical tests | | | |
|---|---|---|---|---|
| Section | Patient group, HBsAg (+) | | Normal group, HBsAg (−) | |
| Positive | TP | 115 | FP | 1 |
| Negative | FN | 3 | TN | 60 |

TP: true positive,
FP: false positive,
TN: true negative,
FN: false negative

According to the test results, 3 persons (about 2.5%) among 118 persons of the patient group were judged false negative and 1 person (about 1.6%) among 61 persons of the normal group was judged false positive. It can be seen from the test results that the diagnostic kit of the present invention provides very accurate diagnosis for hepatitis B infection.

In addition, sensitivity, specificity, and efficiency of the diagnostic kit of the present invention are summarized in Table 10.

TABLE 10

| Section | Result |
|---|---|
| Sensitivity | 97.5% |
| Specificity | 98.4% |
| Efficiency | 97.8% |

Sensitivity: Ratio of true patients in patient group = (TP/(TP + FN)) × 100 (%)
Specificity: Ratio of true normal persons in normal group = (TN/(TN + FP)) × 100 (%)
Efficiency: Ratio of true patients and true normal persons in total group = ((TP + TN)/(TP + TN + FP + FN)) × 100 (%)

As apparent from the above description, a primer set, a method for detecting hepatitis B virus using the primer set, and a hepatitis B virus detection kit including the primer set of the present invention, enable rapid, accurate, and reproducible diagnosis of hepatitis B.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A PCR set consisting of a primer set including a primer consisting of SEQ ID NO: 4 and a primer consisting of SEQ ID NO:6.

2. A method for detecting hepatitis B virus, which comprises amplifying a nucleic acid sample obtained from an organism by PCR using the primer set of claim 1.

3. The method of claim 2, wherein the PCR is a two-step PCR comprising a denaturation step and an annealing and extension step.

4. The method of claim 2, wherein the PCR is performed for 30 minutes or less.

5. The method of claim 2, wherein the PCR is performed on a micro PCR chip.

6. The method of claim 2, wherein the PCR is performed using 0.2-1 µM of each primer and 0.01 pg to 1 µg of a template DNA.

7. The method of claim 2, wherein the PCR is performed under conditions of denaturation at 86-97° C. for 1-30 seconds and annealing and extension at 60-70° C. for 6-30 seconds.

8. The method of claim 5, wherein the micro PCR chip comprises:

a silicon wafer, a surface of which is formed with a PCR chamber made by silicon lithography and the other surface is formed with a heater for heating the PCR chamber; and a glass wafer having an inlet and an outlet.

9. A hepatitis B virus detection kit comprising the primer set of claim 1.

* * * * *